(12) United States Patent
Schneider

(10) Patent No.: US 8,876,873 B2
(45) Date of Patent: *Nov. 4, 2014

(54) BONE PLATE

(71) Applicant: DePuy Synthes Products, LLC, Raynham, MA (US)

(72) Inventor: Rolf Schneider, Solothurn (CH)

(73) Assignee: DePuy Synthes Products, LLC, Raynham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/795,596

(22) Filed: Mar. 12, 2013

(65) Prior Publication Data

US 2013/0190828 A1 Jul. 25, 2013

Related U.S. Application Data

(63) Continuation of application No. 13/713,626, filed on Dec. 13, 2012, which is a continuation of application No. 11/361,941, filed on Feb. 24, 2006, now Pat. No. 8,343,196, which is a continuation of application No. PCT/CH03/00577, filed on Aug. 26, 2003.

(51) Int. Cl.
*A61B 17/80* (2006.01)
*A61L 27/18* (2006.01)

(52) U.S. Cl.
CPC ......... *A61B 17/8033* (2013.01); *A61L 2430/02* (2013.01); *A61B 17/8052* (2013.01); *A61B 17/80* (2013.01); *A61B 17/8057* (2013.01); *A61L 27/18* (2013.01)
USPC ........................................................ 606/286

(58) Field of Classification Search
USPC ....................... 606/70, 71, 280–299, 300–331
See application file for complete search history.

(56) References Cited

U.S. PATENT DOCUMENTS

| | | |
|---|---|---|
| 1,203,546 A | 10/1916 | Parsons |
| 2,228,584 A | 1/1941 | Place |
| 2,443,363 A | 6/1948 | Townsend et al. |
| 2,477,430 A | 7/1949 | Swanstrom |
| 2,846,701 A | 8/1958 | Bedford |
| 3,229,743 A | 1/1966 | Derby |
| 3,263,949 A | 8/1966 | Conrad |

(Continued)

FOREIGN PATENT DOCUMENTS

| | | |
|---|---|---|
| CA | 1112803 | 11/1981 |
| CH | 611147 | 5/1979 |

(Continued)

OTHER PUBLICATIONS

"Cone Drive History and Double Enveloping Technology", http://conedrive.com/history/html., accessed Apr. 20, 2006, 9 pages.

(Continued)

*Primary Examiner* — Christopher Beccia
(74) *Attorney, Agent, or Firm* — Baker & Hostetler LLP

(57) ABSTRACT

A bone plate has an underside on the side of the bone, an upper side and a plurality of holes in the plate connecting the underside with the upper side, with a central hole axis. At least one of these holes in the plate has an internal jacket surface that tapers towards the underside, while the internal jacket surface has N≥3 recesses which extend radially away from the axis of the hole.

24 Claims, 3 Drawing Sheets

(56) References Cited

U.S. PATENT DOCUMENTS

| | | |
|---|---|---|
| 3,314,326 A | 4/1967 | Bedford |
| 3,364,807 A | 1/1968 | Holton |
| 3,388,732 A | 6/1968 | Holton |
| 3,463,148 A | 8/1969 | Treace |
| 3,551,389 A | 12/1970 | Prince et al. |
| 3,552,389 A | 1/1971 | Allgower et al. |
| 3,630,261 A | 12/1971 | Gley |
| 3,668,972 A | 6/1972 | Allgower et al. |
| 3,695,618 A | 10/1972 | Woolley et al. |
| 3,716,050 A | 2/1973 | Johnston |
| 3,741,205 A | 6/1973 | Markolf et al. |
| 3,744,488 A | 7/1973 | Cox |
| 3,779,240 A | 12/1973 | Kondo |
| 3,877,339 A | 4/1975 | Muenchinger |
| RE28,841 E | 6/1976 | Allgower et al. |
| 3,967,049 A | 6/1976 | Brandt |
| 3,996,834 A | 12/1976 | Reynolds |
| 4,029,091 A | 6/1977 | Von Bezold et al. |
| 4,175,555 A | 11/1979 | Herbert |
| 4,219,015 A | 8/1980 | Steinemann |
| 4,263,904 A | 4/1981 | Judet |
| 4,304,039 A | 12/1981 | Asmus |
| 4,338,926 A | 7/1982 | Kummer et al. |
| 4,355,198 A | 10/1982 | Gartland, Jr. |
| 4,408,601 A | 10/1983 | Wenk |
| 4,429,690 A | 2/1984 | Angelino-Pievani |
| RE31,628 E | 7/1984 | Allgower et al. |
| 4,484,570 A | 11/1984 | Sutter et al. |
| 4,491,317 A | 1/1985 | Bansal |
| 4,493,317 A | 1/1985 | Klaue |
| 4,513,744 A | 4/1985 | Klaue |
| 4,565,193 A | 1/1986 | Streli |
| 4,612,923 A | 9/1986 | Kronenthal |
| 4,630,985 A | 12/1986 | Simons |
| 4,651,724 A | 3/1987 | Berentey et al. |
| 4,683,878 A | 8/1987 | Carter |
| 4,717,613 A | 1/1988 | Ottaviano |
| 4,776,329 A | 10/1988 | Treharne |
| 4,781,183 A | 11/1988 | Casey et al. |
| 4,794,918 A | 1/1989 | Wolter |
| 4,838,252 A | 6/1989 | Klaue |
| 4,858,601 A | 8/1989 | Glisson |
| 4,867,144 A | 9/1989 | Karas et al. |
| 4,927,421 A | 5/1990 | Goble et al. |
| 4,957,497 A | 9/1990 | Hoogland et al. |
| 4,988,350 A | 1/1991 | Herzberg |
| 5,002,544 A | 3/1991 | Klaue et al. |
| 5,006,120 A | 4/1991 | Carter |
| 5,027,904 A | 7/1991 | Miller et al. |
| 5,039,265 A | 8/1991 | Rath et al. |
| 5,041,113 A | 8/1991 | Biedermann et al. |
| 5,041,114 A | 8/1991 | Chapman et al. |
| 5,053,036 A | 10/1991 | Perren et al. |
| 5,085,660 A | 2/1992 | Lin |
| 5,108,399 A | 4/1992 | Eitenmuller et al. |
| 5,129,901 A | 7/1992 | Decoste |
| 5,147,361 A | 9/1992 | Ojima et al. |
| 5,151,103 A | 9/1992 | Tepic et al. |
| 5,190,544 A | 3/1993 | Chapman et al. |
| 5,197,966 A | 3/1993 | Sommerkamp |
| 5,261,910 A | 11/1993 | Warden et al. |
| 5,269,784 A | 12/1993 | Mast |
| 5,275,601 A * | 1/1994 | Gogolewski et al. ......... 606/291 |
| 5,304,180 A | 4/1994 | Slocum |
| 5,306,275 A | 4/1994 | Bryan |
| 5,324,290 A | 6/1994 | Zdeblick et al. |
| 5,336,224 A | 8/1994 | Selman |
| 5,360,448 A | 11/1994 | Thramann |
| 5,364,398 A | 11/1994 | Chapman et al. |
| 5,364,399 A | 11/1994 | Lowery et al. |
| 5,403,136 A | 4/1995 | Mathys |
| 5,429,641 A | 7/1995 | Gotfried |
| 5,514,138 A | 5/1996 | McCarthy |
| 5,534,032 A | 7/1996 | Hodorek |
| 5,558,674 A | 9/1996 | Heggeness et al. |
| 5,571,198 A | 11/1996 | Drucker et al. |
| 5,591,168 A | 1/1997 | Judet et al. |
| 5,601,551 A | 2/1997 | Taylor et al. |
| 5,601,553 A | 2/1997 | Trebing et al. |
| 5,607,426 A | 3/1997 | Ralph et al. |
| 5,607,428 A | 3/1997 | Lin |
| 5,620,445 A | 4/1997 | Brosnahan et al. |
| 5,674,222 A | 10/1997 | Berger et al. |
| 5,702,399 A | 12/1997 | Kilpela et al. |
| 5,709,686 A | 1/1998 | Talos et al. |
| 5,741,258 A | 4/1998 | Klaue et al. |
| 5,749,872 A | 5/1998 | Kyle et al. |
| 5,772,662 A | 6/1998 | Chapman et al. |
| 5,785,713 A | 7/1998 | Jobe |
| 5,810,823 A | 9/1998 | Klaue et al. |
| 5,938,664 A | 8/1999 | Winquist et al. |
| 5,954,722 A | 9/1999 | Bono |
| 5,961,524 A | 10/1999 | Crombie |
| 5,968,047 A | 10/1999 | Reed |
| 5,976,141 A | 11/1999 | Haag |
| 5,999,940 A | 12/1999 | Ranger |
| 6,001,099 A | 12/1999 | Huebner |
| 6,022,352 A | 2/2000 | Vandewalle |
| 6,030,162 A | 2/2000 | Huebner |
| 6,030,389 A | 2/2000 | Wagner et al. |
| 6,096,040 A | 8/2000 | Esser |
| 6,129,730 A | 10/2000 | Bono et al. |
| 6,152,927 A | 11/2000 | Farris et al. |
| 6,183,475 B1 | 2/2001 | Lester et al. |
| 6,206,881 B1 | 3/2001 | Frigg et al. |
| 6,228,085 B1 | 5/2001 | Theken et al. |
| 6,261,291 B1 | 7/2001 | Talaber et al. |
| 6,306,136 B1 | 10/2001 | Baccelli |
| 6,322,562 B1 | 11/2001 | Wolter |
| 6,342,055 B1 | 1/2002 | Eisermann et al. |
| 6,348,052 B1 | 2/2002 | Sammarco |
| 6,364,882 B1 | 4/2002 | Orbay |
| 6,423,064 B1 | 7/2002 | Kluger |
| 6,440,135 B2 | 8/2002 | Orbay et al. |
| 6,454,769 B2 | 9/2002 | Wagner et al. |
| 6,454,770 B1 | 9/2002 | Klaue |
| 6,468,278 B1 | 10/2002 | Muckter |
| 6,527,776 B1 | 3/2003 | Michelson |
| 6,565,569 B1 | 5/2003 | Assaker et al. |
| 6,575,975 B2 | 6/2003 | Brace et al. |
| D479,331 S | 9/2003 | Pike et al. |
| 6,623,486 B1 | 9/2003 | Weaver et al. |
| 6,669,701 B2 | 12/2003 | Steiner et al. |
| 6,719,759 B2 | 4/2004 | Wagner et al. |
| 6,730,091 B1 | 5/2004 | Pfefferle et al. |
| 6,893,443 B2 | 5/2005 | Frigg et al. |
| 6,955,677 B2 | 10/2005 | Dahners |
| 6,974,461 B1 | 12/2005 | Wolter |
| 7,044,953 B2 | 5/2006 | Capanni |
| 7,128,744 B2 | 10/2006 | Weaver et al. |
| 7,179,260 B2 | 2/2007 | Gerlach et al. |
| 7,309,340 B2 | 12/2007 | Fallin et al. |
| 7,338,491 B2 | 3/2008 | Baker et al. |
| 7,341,589 B2 | 3/2008 | Weaver et al. |
| 7,354,441 B2 | 4/2008 | Frigg |
| 7,537,596 B2 | 5/2009 | Jensen |
| 7,637,928 B2 | 12/2009 | Fernandez |
| 7,695,502 B2 | 4/2010 | Orbay et al. |
| 7,776,916 B2 | 8/2010 | Freeman et al. |
| 8,075,561 B2 | 12/2011 | Wolter |
| 8,118,846 B2 | 2/2012 | Leither et al. |
| 8,343,196 B2 * | 1/2013 | Schneider ...................... 606/286 |
| 2002/0156474 A1 | 10/2002 | Wack et al. |
| 2004/0073218 A1 | 4/2004 | Dahners |
| 2004/0260306 A1 | 12/2004 | Fallin et al. |
| 2005/0015089 A1 * | 1/2005 | Young et al. ..................... 606/69 |
| 2005/0107796 A1 | 5/2005 | Gerlach et al. |
| 2005/0165400 A1 * | 7/2005 | Fernandez ....................... 606/69 |
| 2005/0261688 A1 | 11/2005 | Grady et al. |
| 2006/0004361 A1 | 1/2006 | Hayeck et al. |
| 2006/0217722 A1 | 9/2006 | Dutoit et al. |
| 2006/0235400 A1 | 10/2006 | Schneider |
| 2007/0016205 A1 | 1/2007 | Beutter et al. |
| 2007/0088360 A1 | 4/2007 | Orbay et al. |

(56) References Cited

U.S. PATENT DOCUMENTS

| | | |
|---|---|---|
| 2007/0162016 A1 | 7/2007 | Matityahu |
| 2007/0206244 A1 | 9/2007 | Kobayashi |
| 2007/0260244 A1 | 11/2007 | Wolter |
| 2008/0140130 A1 | 6/2008 | Chan et al. |
| 2008/0208259 A1 | 8/2008 | Gilbert et al. |
| 2008/0234749 A1 | 9/2008 | Forstein |
| 2008/0300637 A1 | 12/2008 | Austin et al. |
| 2009/0018557 A1 | 1/2009 | Pisharodi |
| 2009/0018588 A1 | 1/2009 | Eckhof et al. |
| 2009/0076553 A1 | 3/2009 | Wolter |
| 2009/0076554 A1 | 3/2009 | Huebner et al. |
| 2009/0118768 A1 | 5/2009 | Sixto et al. |
| 2009/0143824 A1 | 6/2009 | Austin et al. |
| 2009/0143825 A1 | 6/2009 | Graham et al. |
| 2009/0292318 A1 | 11/2009 | White et al. |
| 2009/0312803 A1 | 12/2009 | Austin et al. |
| 2010/0016858 A1 | 1/2010 | Michel |
| 2010/0030277 A1 | 2/2010 | Haidukewych et al. |
| 2010/0057086 A1 | 3/2010 | Price et al. |
| 2010/0076496 A1 | 3/2010 | Fernandez |
| 2010/0094357 A1 | 4/2010 | Wallenstein et al. |
| 2010/0100134 A1 | 4/2010 | Mocanu |
| 2010/0137919 A1 | 6/2010 | Wolter |
| 2010/0274296 A1 | 10/2010 | Appenzeller et al. |
| 2010/0312286 A1 | 12/2010 | Dell'Oca |
| 2011/0224671 A1 | 9/2011 | Koay |

FOREIGN PATENT DOCUMENTS

| | | |
|---|---|---|
| CH | 672245 | 11/1989 |
| CH | 675531 | 10/1990 |
| DE | 3442004 | 4/1986 |
| DE | 4341980 | 6/1995 |
| DE | 4343117 | 6/1995 |
| DE | 4438264 | 3/1996 |
| DE | 19629011 | 1/1998 |
| DE | 9321544 | 10/1999 |
| DE | 19832513 | 2/2000 |
| DE | 20309361 | 9/2003 |
| DE | 20317651 | 3/2004 |
| DE | 10-2005-042766 | 1/2007 |
| EP | 0053999 | 6/1982 |
| EP | 158030 | 10/1985 |
| EP | 0207884 | 1/1987 |
| EP | 241914 | 10/1987 |
| EP | 0360139 | 3/1990 |
| EP | 0410309 | 1/1991 |
| EP | 0266146 | 12/1992 |
| EP | 0515828 | 12/1992 |
| EP | 0530585 | 3/1993 |
| EP | 0848600 | 6/1998 |
| EP | 1468655 | 10/2004 |
| EP | 1604619 | 12/2005 |
| EP | 1658015 | 5/2006 |
| EP | 1712197 | 10/2006 |
| EP | 1741397 | 1/2007 |
| EP | 1767160 | 3/2007 |
| FR | 742618 | 3/1933 |
| FR | 2233973 | 1/1975 |
| FR | 2405062 | 5/1979 |
| FR | 2405705 | 5/1979 |
| FR | 2405706 | 5/1979 |
| FR | 2496429 | 6/1982 |
| FR | 2674118 | 9/1992 |
| GB | 997733 | 7/1965 |
| GB | 1237405 | 6/1971 |
| GB | 1250413 | 10/1971 |
| GB | 1312189 | 4/1973 |
| GB | 1385398 | 2/1975 |
| GB | 1575194 | 9/1980 |
| JP | H11-512004 | 10/1999 |
| JP | 11299804 | 11/1999 |
| JP | 2001-525701 | 12/2001 |
| JP | 2001-525702 | 12/2001 |
| JP | 2002-232185 | 8/2002 |
| JP | 2002-542875 | 12/2002 |
| JP | 2003-509107 | 3/2003 |
| SU | 1037911 | 8/1983 |
| SU | 1279626 | 12/1986 |
| WO | WO 87/00419 | 1/1987 |
| WO | WO 87/06982 | 11/1987 |
| WO | WO 88/03781 | 6/1988 |
| WO | WO 96/29948 | 10/1996 |
| WO | WO 97/09000 | 3/1997 |
| WO | WO 98/51226 | 11/1998 |
| WO | WO 00/53110 | 9/2000 |
| WO | WO 00/53111 | 9/2000 |
| WO | WO 00/66012 | 11/2000 |
| WO | WO 01/19267 | 3/2001 |
| WO | WO 01/54601 | 8/2001 |
| WO | WO 02/096309 | 12/2002 |
| WO | WO 2004/089233 | 10/2004 |
| WO | WO 2005/018472 | 3/2005 |
| WO | WO 2007/014279 | 2/2007 |
| WO | WO 2007/108734 | 9/2007 |
| WO | WO 2009/023666 | 2/2009 |
| WO | WO 2009/058969 | 5/2009 |
| WO | WO 2011/032140 | 3/2011 |

OTHER PUBLICATIONS

"Multiple Offerings of Plates, Screws and Pegs," Small Bone Innovations, Inc., Dec. 2009, 3 pages.
ACE Symmetry, "Curves in All the Right Places," 1996, 3 pages.
European Patent Application No. 12006606: Extended European Search Report dated Jan. 21, 2013, 8 pages.
European Patent Application No. 12006615: Extended European Search Report dated Jan. 21, 2013, 7 pages.
European Patent Application No. 12006617: Extended European Search Report dated Jan. 21, 2013, 8 pages.
International Search Report for International Application No. PCT/CH03/00577 dated Apr. 28, 2004, German Language version.
International Search Report for International Application No. PCT/CH03/00577 dated Apr. 28, 2004, English language translation of the German language version.
Stryker, "VariAx Distal Radius: Locking Plate System", www.osteosynthesis.stryker.com, 2006, 12 pages.

* cited by examiner

BONE PLATE

CROSS REFERENCE TO RELATED APPLICATIONS

This application is a continuation of U.S. patent application Ser. No. 13/713,626, filed Dec. 13, 2012, which is a continuation of U.S. patent application Ser. No. 11/361,942, filed Feb. 24, 2006, now U.S. Pat. No. 8,343,196, issued on Jan. 1, 2013, which is a continuation of International Patent Application No. PCT/CH2003/000577, filed Aug. 26, 2003, the entire contents of which are expressly incorporated herein by reference thereto.

FIELD OF THE INVENTION

The invention relates to a bone plate for use in repairing bone fractures.

BACKGROUND OF THE INVENTION

Bone plates are known in the art and may be indicated for the entire skeleton. Particularly significant are, however, the usual large and small fragment indications for surgically treating bone breakages.

From DE-A 198 32 513 a bone plate of the generic type is known. In the case of this known device, the angular alignment of the bone screws relative to the bone plate and their angularly stable fixing is achieved by a ring arranged between the head of the screw and the hole in the plate. A disadvantage of this construction is, on the one hand, the more expensive manufacture with an additional component (ring) and the danger that the tiny ring will fall out or be pushed out from the hole in the plate, thus making the device unusable, and, on the other hand, the more expensive OP technique because the axis of the ring has to be correspondingly aligned before inserting the screw.

The present invention seeks to remedy this problem. The object of the invention is to produce a bone plate, without the need for additional components, that can accommodate conventional locking capscrews in an angularly and axially stable manner

SUMMARY OF THE INVENTION

The invention achieves this objective with a bone plate having an upper surface, a lower surface, and at least one hole extending from the upper surface to the lower surface, the at least one hole having a central hole axis and an internal jacket surface. The internal jacket surface includes N recesses extending radially away from the central axis, where N≥3. The internal jacket surface may also include surface projections on at least a portion of the internal jacket surface.

The advantage achieved by the invention is essentially that as a result of the bone plate according to the invention a bone screw can be introduced at an angle that is different from the specified axis of the hole (usually at right angles to the plane of the bone plate) and secured in this position, without significantly sacrificing the stability, as is the case in known devices.

By virtue of the at least three recesses in the internal jacket surface of the holes in the plate, centralizing bearing surfaces are produced for the capscrew, even when the bone screw is inclined, and the bearing surfaces result in an even distribution of the load. In the case of bone screws with a threaded head and holes in the plate with an inner thread, when the screw is inclined, the threaded head can "jump over" the pitches of the thread in the hole of the plate interrupted by the recesses, without "cutting through" them.

A further advantage of the bone plate according to the invention is the possibility to use the at least three recesses in the hole in the plate to guide drilling bushings or guide bushings, by which the bone screws can be guided during their insertion. In this case the drilling bushings or guide bushings no longer need to be screwed into the holes in the plate (as is the case in the state-of-the-art), but due to the recesses need only to be inserted into the holes in the plate, resulting in a simple manner in the centre and direction of the axis of the hole. All that is required for this purpose is that the tips of the cannulated drilling bushings or guide bushings need to have the negative geometry of the holes in the plate, without any thread or other, similarly acting, structures. A snap-in mechanism may possibly be used in conjunction.

In one particular embodiment, the internal jacket surface of the hole in the plate is provided with a three-dimensional structure, which serves the purpose of guiding of a correspondingly structured capscrew. The three-dimensional structure is macroscopic and preferably comprises partial or complete pitches of a thread, ribs or protuberations. The internal jacket surface may be a multi-start thread.

The geometry of the surface of the N "locking leg", formed by the N recesses, is advantageously constructed to facilitate compatibility with the bone screw to be introduced. This can be in the form of a classic helical thread, a thread-like shape with or without pitch or also only a certain number of grooves or ribs, or also a quasi-thread with or without pitch. The number of grooves or ribs is preferably always odd (e.g. 3, 5, 7 or 9).

The internal jacket surface can have a concave, preferably spherical, tapered or ellipsoidal shape. This shape facilitates the insertion of a bone screw in such a manner that at the first contact of the bone screw with the internal jacket surface the bone screw is automatically pulled into the hole in the plate, without exerting prior a compression force on the bone via the bone plate, as is partly the case with devices known in the art.

In the case of a further development, at least one of the holes in the plate is constructed as an oblong hole.

The N recesses are arranged at a distance of 360°/N relative to the central axis. The recesses preferably have a peripheral expansion of at least 1° and a maximum of 119°. At the same time the N recesses divide the internal jacket surface into N sections of the jacket surface.

In the case of a particular embodiment the recesses extend exclusively within the internal jacket surface. In the case of another embodiment, the recesses extend radially away from the axis of the hole past the internal jacket surface.

The recesses may extend cylindrically or tapered from the upper side to the underside. The advantage of this is, that the recesses can be used for the fixing of a drilling bushing for pre-drilling or for the insertion of the Kirschner wires. Thus the drilling bushing no longer has to be screwed into the hole in the plate, only to be inserted without damaging the bearing area for the screw.

The recesses can extend from the upper side to the underside over the entire height of the bone plate.

The bone plate can be made from steel or titanium or also from a plastic material. In the case of plastic plates from polyacryl etherketone (PEAK) or polyether etherketone (PEEK) with an elongation at break of 40-70% and a modulus of elasticity of 3000-6000 N/mm$^2$ are preferred. However, polysulphon, having an elongation at break of 80-120% and a modulus of elasticity of 2000-3500 N/mm$^2$ may also be used. Furthermore, liquid crystal polymer (LCP) having an elongation at break of 1.5-2.5% and a modulus of elasticity of 5000-20000 N/mm$^2$ may be suitable. Finally, polyoxymethylene (POM) with an elongation at break of 10-50% and a modulus of elasticity of 2000-3500 N/mm$^2$ and polyphenylene sulphide (PPS) having an elongation at break of 0.2-1.0% and a modulus of elasticity of 12000-20000 N/mm$^2$ may be used.

Bone plates from plastic material may be reinforced with metal, plastic or carbon fibres.

Various bone screws can be used with the bone plates. For example, those having a convex, preferably spherical or tapered head portion. The head portion of the bone screws may also have a three-dimensional structure. In the case of a special embodiment the head portion of the bone screw is made from a material that is harder than the internal jacket surface of the bone plate. The internal jacket surface of the bone plate and the head portion of the bone screw have preferably matching threads.

In the case of a plastic plate, the holes in the plate may be executed as metallic thread inserts. Conversely, in the case of a metal bone plate the holes in the plate are executed as polymer thread inserts.

BRIEF DESCRIPTION OF THE DRAWINGS

The invention and developments of the invention are explained in detail based on the partly schematic illustrations of several embodiments in the figures, wherein.

DETAILED DESCRIPTION OF THE PREFERRED EMBODIMENTS

Figure 1:
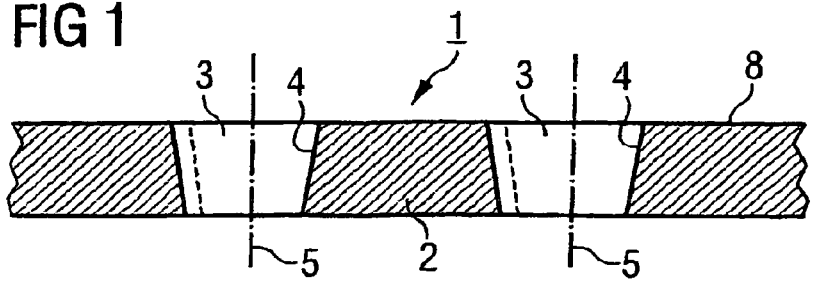
FIG. 1 shows a longitudinal section through a bone plate with tapered holes in the plate.
Figure 3:
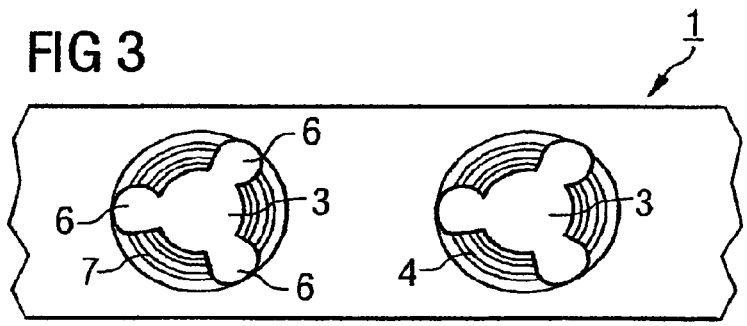
FIG. 3 shows a top view of a bone plate with three recesses in the internal jacket surface of the holes in the plate.

The bone plate 1 illustrated in FIGS. 1 and 3 has an underside 2 on the side of the bone, an upper side 8 and a plurality of holes 3 in the plate connecting the underside 2 with the upper side 8, the holes having a central hole axis 5. The holes 3 in the plate have an internal jacket surface 4 that tapers towards the underside 2. Furthermore, the internal jacket surface 4 has three recesses 6 which extend radially away from the hole axis 5 of the hole at a uniform distance of 120° from one another. Their peripheral expansion is approximately 40° and they extend exclusively within the internal jacket surface 4. The recesses 6 extend tapered over the entire height of the bone plate 1 from the upper side 8 to the underside 2. In addition, the internal jacket surface 4 is provided with a three-dimensional structure 7 in the form of a thread.

Figure 4:
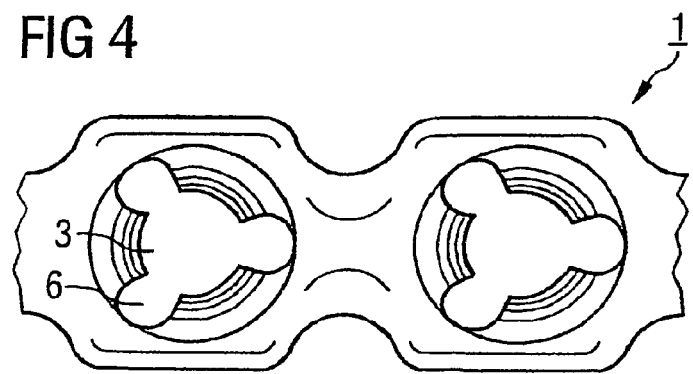
FIG. 4 shows a variation of the bone plate according to FIG. 3 with larger recesses in the internal jacket surface of the holes in the plate.

FIG. 4 illustrates a variation of the execution according to FIG. 3, wherein the recesses extend radially away from the axis of the hole past the internal jacket surface.

Figure 2:
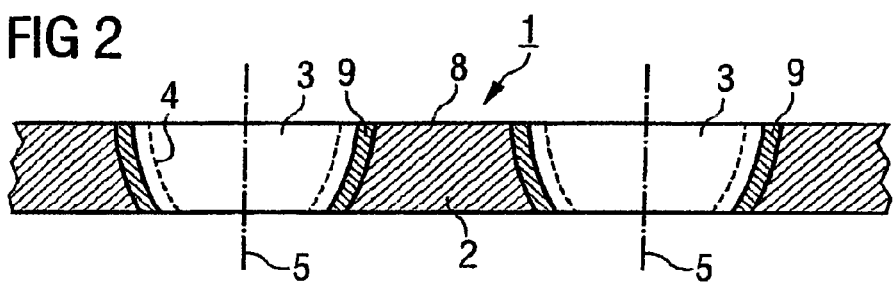
FIG. 2 shows a longitudinal section through a bone plate with spherical holes in the plate.
Figure 5:
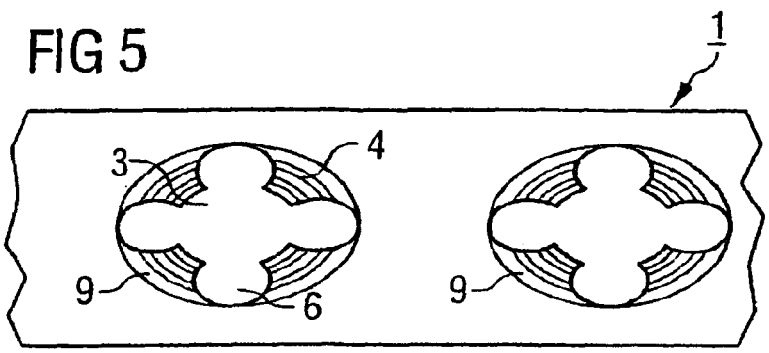
FIG. 5 shows a top view of a bone plate with thread inserts with four recesses in the internal jacket surface of the elliptic holes in the plate.

FIGS. 2 and 5 illustrate a further alternative embodiment, wherein the holes 3 in the plate are constructed as oblong holes. The bone plate is made basically from a plastic material (PEEK) with embedded metallic thread inserts 9 from titanium, forming the holes 3 in the plate. In the case of this embodiment the holes 3 in the plate have four recesses 6, which extend radially away from the axis 5 of the hole past the internal jacket surface 4. The internal jacket surface 4 is divided into four sections of the jacket surface. The recesses extend tapered over the entire height of the bone plate 1 from the upper side 8 to the underside 2. In addition, the internal jacket surface 4 is provided with a three-dimensional structure 7 in the form of a multi-start thread. As far as material is concerned, this embodiment may also be inverted, whereby the bone plate is basically made from metal (titanium) and the embedded therein thread inserts 9 are made from plastic material (PEEK), forming the holes 3 in the plate.

Figure 6:
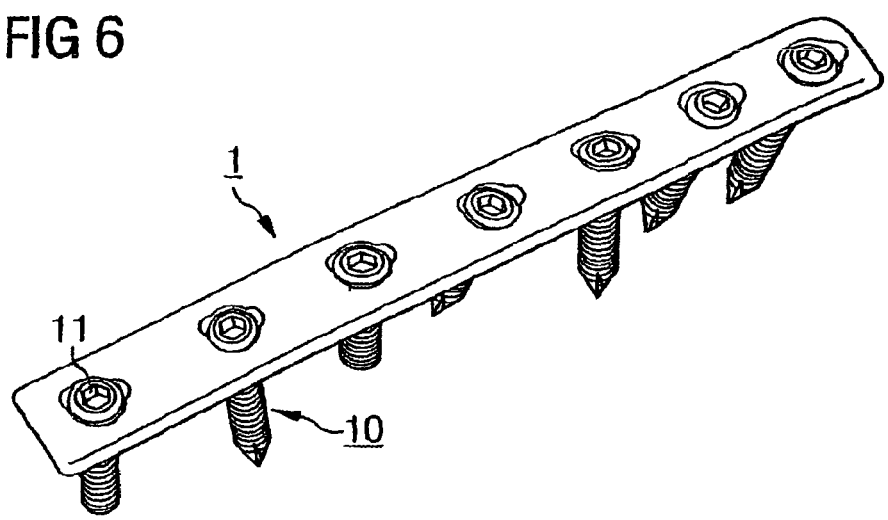
FIG. 6 shows a perspective view of a bone plate according to FIG. 1 from above with the bone screws inserted.
Figure 7:
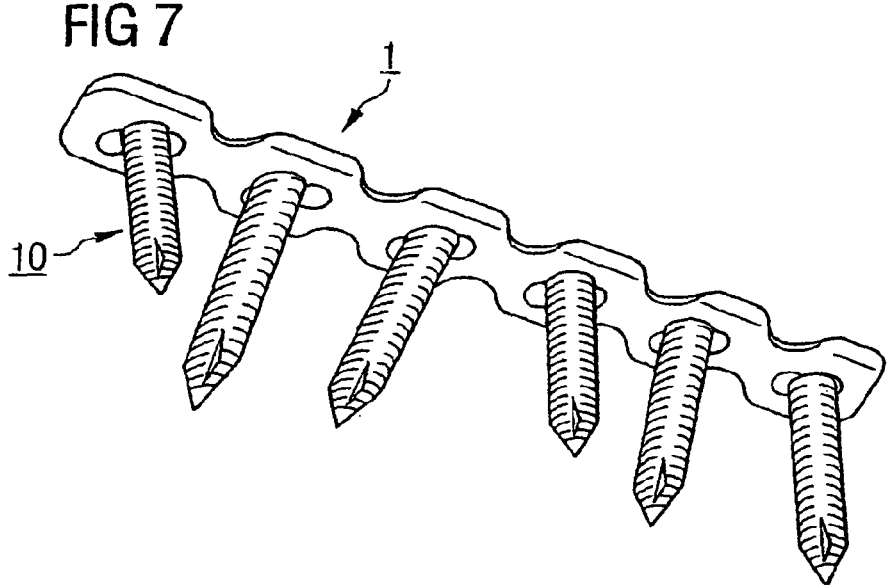
FIG. 7 shows a perspective view of a bone plate according to FIG. 1 from below with the bone screws inserted.

FIG. 6 illustrates the bone plate according to FIG. 1, with bone screws 10 inserted from above, the head portions 11 of which are spherical. FIG. 7 shows the same bone plate 1 from below.

Figure 8:
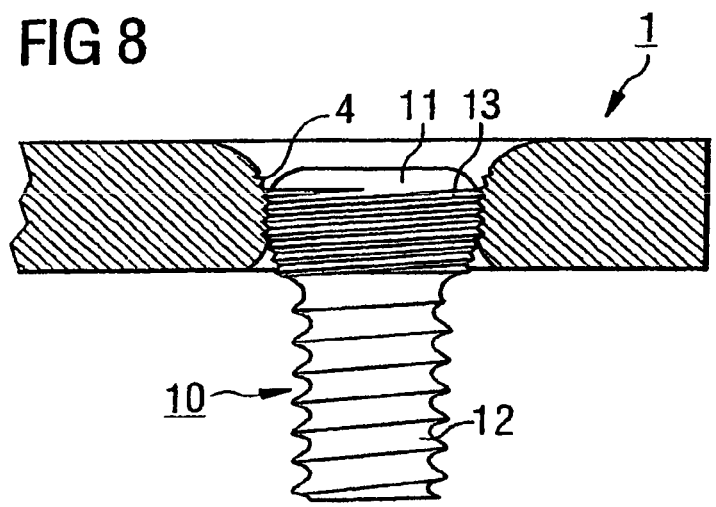
FIG. 8 shows a longitudinal section through a bone plate with a bone screw inserted without angular misalignment.

In FIG. 8, a bone plate 1 is illustrated with bone screws 10 inserted therein without angular misalignment. The internal jacket surface 4 of the hole of the bone plate 1 and the head portion 11 of the bone screw 10 have matching threads 13.

Figure 9:
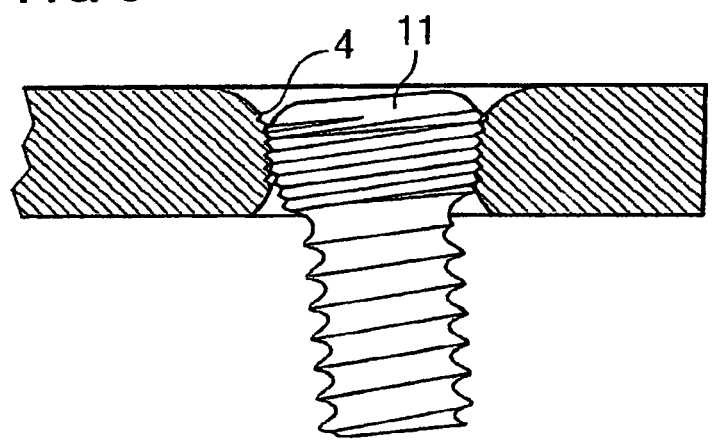
FIG. 9 shows a longitudinal section through a bone plate with a bone screw inserted with angular misalignment.

FIG. 9 illustrates the same variation as FIG. 8, while the bone screw 10 is angularly misaligned.

While the present invention has been described with reference to the preferred embodiments, those skilled in the art will recognize that numerous variations and modifications may be made without departing from the scope of the present invention. Accordingly, it should be clearly understood that the embodiments of the invention described above are not intended as limitations on the scope of the invention, which is defined only by the following claims.

What is claimed:

1. A bone plate comprising:
a lower surface configured to face a bone;
an upper surface facing opposite the lower surface; and
at least one hole extending from the upper surface to the lower surface, the at least one hole having a central axis and an internal jacket surface, wherein the internal jacket surface includes N recesses extending radially away from the central axis, wherein N≥3 and the internal jacket surface includes surface projections on at least a portion of the internal jacket surface that mate with threads of a head of a bone fixation element as the bone fixation element is rotationally inserted through the at least one hole at a user selected angle within a permitted range of angles relative to the central axis, and at least a first one of the recesses extending between the upper surface and the lower surface.

2. The bone plate of claim 1, wherein the first one of the recesses extends through an entire thickness of the bone plate from the upper surface to the lower surface.

3. The bone plate of claim 2, wherein a second one of the recesses extends through the entire thickness of the bone plate.

4. The bone plate of claim 1, wherein the recesses have a curved shape such that the recesses are concave with respect to the central axis.

5. The bone plate of claim 1, wherein the internal jacket surface tapers towards the lower surface of the plate.

6. The bone plate of claim 1, wherein the internal jacket surface has a concave shape with respect to the central axis.

7. The bone plate of claim 1, wherein the internal jacket surface has a spherical or ellipsoidal shape.

8. The bone plate of claim 1, wherein the hole is oblong in shape.

9. The bone plate of claim 1, wherein the surface projections are threads or ribs.

10. The bone plate of claim 1, wherein each of the recesses include a center, and the centers of the recesses are angularly spaced at a distance of 360°/N about the central axis of the hole.

11. The bone plate of claim 1, wherein each recess has a peripheral expansion of at least 1°.

12. The bone plate of claim 1, wherein each recess has a maximum peripheral expansion of 119°.

13. The bone plate of claim 1, wherein the recesses extend exclusively within the internal jacket surface of the hole.

14. The bone plate of claim 1, wherein the recesses extend radially away from the axis of the hole beyond the internal jacket surface.

15. The bone plate of claim 1, wherein the surface projections on the internal jacket surface of the hole are formed in a direction substantially perpendicular to the central axis of the hole.

16. The bone plate of claim 1, wherein the plate is formed of a metal, plastic or carbon fibre reinforced plastic material.

17. A bone plate comprising:
a lower surface configured to face a bone;
an upper surface that faces opposite the lower surface;
a plate thickness defined by the upper and lower surfaces;
at least one hole extending from the upper surface to the lower surface, each of the at least one hole having a respective central hole axis, periphery, and internal surface;
a plurality of surface projections on the internal surface of the hole that mate with a threaded head of a bone fixation element as the bone fixation element is rotationally inserted through the at least one hole at a user selected angle within a permitted range of angles relative to the central hole axis, the projections oriented generally perpendicular to the central axis of the hole; and
at least three recesses in the internal surface of the hole angularly spaced about the periphery and extending radially away from the central axis.

18. The bone plate of claim 17, wherein a first one of the recesses extends from the upper surface to the lower surface through the entire plate thickness.

19. The bone plate of claim 17, wherein the internal surface of the hole tapers towards the lower surface of the plate.

20. A bone plate comprising:
a lower surface configured to face a bone;
an upper surface that faces opposite the lower surface; and
a plurality of plate holes connecting the lower surface with the upper surface, each plate hole having a respective central hole axis, inner surface, and threading,
wherein each inner surface has N≥3 recesses that extend away from the hole axis and divide the threading into threaded sections, a first one of the recesses extending through an entire thickness of the bone plate from the upper surface to the lower surface, and
wherein the threading and the recesses are configured such that threads of a threaded head of a bone screw jump over the threading of the one of the plurality of plate holes without cutting into the inner surface when the screw is inserted at a selected one of a plurality of angles with respect to the central hole axis.

21. A bone plate comprising:
a lower surface configured to face a bone;
an upper surface facing opposite the lower surface; and
a plurality of plate holes each defined by a respective inner surface that connects the lower surface with the upper surface, each plate hole having a respective central hole axis;
wherein each inner surface has N≥3 recesses that extend away from the hole axis, each of the recesses disposed between adjacent ones of a plurality of threaded sections, and at least a first one of the recesses of each of the plate holes extending between the lower surface and the upper surface.

22. The bone plate of claim 21, wherein each of the recesses of each of the bone holes has a respective peripheral expansion, each of the threaded sections has a respective peripheral expansion, and the peripheral expansion of each of the recesses is no less than the peripheral expansion of the adjacent ones of the plurality of threaded sections.

23. The bone plate of claim 21, wherein each of the threaded sections mates with a threaded head of a bone screw that is rotationally inserted into the respective plate hole at a select angle within a permitted range of angles.

24. The bone plate of claim 21, wherein at least a first one of the recesses of each of the plate holes extends through an entire thickness of the bone plate from the upper surface to the lower surface.

* * * * *